United States Patent
Sanders et al.

(10) Patent No.: US 7,666,435 B2
(45) Date of Patent: *Feb. 23, 2010

(54) TREATMENT OF FINE WRINKLES WITH CLOSTRIDIA NEUROTOXINS

(76) Inventors: Ira Sanders, 607 72nd St., North Bergen, NJ (US) 07047; Rosemary Aquila-Sanders, 607 72nd St., North Bergen, NJ (US) 07047

(*) Notice: Subject to any disclaimer, the term of this patent is extended or adjusted under 35 U.S.C. 154(b) by 0 days.

This patent is subject to a terminal disclaimer.

(21) Appl. No.: 11/852,414

(22) Filed: Sep. 10, 2007

(65) Prior Publication Data

US 2008/0112981 A1    May 15, 2008

Related U.S. Application Data

(63) Continuation-in-part of application No. 10/524,304, filed as application No. PCT/US03/25708 on Aug. 18, 2003, now Pat. No. 7,288,259.

(60) Provisional application No. 60/404,378, filed on Aug. 19, 2002.

(51) Int. Cl.
*A61K 39/08* (2006.01)
*A61K 38/16* (2006.01)

(52) U.S. Cl. .................. 424/239.1; 424/236.1; 424/9.1; 514/2; 514/12; 530/350; 435/252.7

(58) Field of Classification Search .............. 424/239.1, 424/236.1, 9.1; 514/2, 12; 530/350; 435/252.7
See application file for complete search history.

(56) References Cited

U.S. PATENT DOCUMENTS

| | | | | |
|---|---|---|---|---|
| 7,288,259 | B2 * | 10/2007 | Sanders et al. | 424/239.1 |
| 2004/0009180 | A1 * | 1/2004 | Donovan | 424/184.1 |
| 2005/0074466 | A1 * | 4/2005 | Suskind et al. | 424/247.1 |
| 2008/0081049 | A1 * | 4/2008 | Sanders | 424/239.1 |

OTHER PUBLICATIONS

Letessier, J. Dermatol. Treat. 10, 31-36 (1999).*
Becker-Wegerich et al., Clinical and Experimental Dermatology 26, 619-630 (2001).*

* cited by examiner

*Primary Examiner*—Chih-Min Kam
(74) *Attorney, Agent, or Firm*—Omri M. Behr

(57) ABSTRACT

Methods of using clostridial toxins and other biological agents to thin skin and control fine wrinkles in humans are provided. In preferred embodiments the methods provide beneficial effects in humans.

19 Claims, No Drawings

TREATMENT OF FINE WRINKLES WITH CLOSTRIDIA NEUROTOXINS

RELATED APPLICATIONS

This application is a continuation in part of U.S. patent application Ser. No. 10/524304, filed Feb. 8, 2005, now U.S. Pat. No. 7,288,259, which is a 371 of PCT/US03/25708, filed Aug. 18, 2003, which claims priority of U.S. Provisional Application Ser. No. 60/404,378, filed Aug. 19, 2002.

FIELD OF THE INVENTION

This invention relates to methods and compositions for thinning the skin and treating fine wrinkling of skin, by administration of clostridia neurotoxins in particular Botulinum Toxin.

BACKGROUND OF THE INVENTION

Throughout this application various publications are referred to as references, within parentheses or by footnote. The procedures set forth in these publications where relevant are hereby incorporated by reference. The reasoning set therein is also incorporated by reference in so far as it does not differ from or conflict with the text herein. In case of such difference or conflict the text herein controls.

Cells contain vesicles (also called endosomes) that are spherical structures with a bilipid membrane. These endosomes can merge with the cell membrane and release their content into the extracellular environment (exocytosis). The process of forming vesicles and merging them with cellular membranes can be broadly divided into two categories: constitutive and regulated. Constitutive exocytoses are maintenance functions of the cell while regulated exocytoses is a specialized response of the cell to an external or internal signal. The paradigm of specialized regulated secretion is the release of neurotransmitters at neuronal synapses. At the proper signal (usually a drop in cell voltage) hundreds of vesicles merge with the cell membrane to release their neurotransmitters. The neurotransmitters diffuse across the synaptic space to bind to and excite the postsynaptic membrane of a second neuron.

Exocytosis requires specialized proteins on the vesicle and presynaptic membrane that are collectively known as the SNARE proteins. Removal of any of these proteins can stop vesicle docking to membrane and block or decrease neural signaling. One protein on the vesicle membrane called VAMP (vesicle associated membrane protein) and one on the presynaptic membrane called SNAP (synapse associated protein) are the targets of the botulinum and tetanus neurotoxins from the Clostridial bacterium.

Botulinum toxin (BT) is a potent neurotoxin produced by the anaerobic gram-positive bacterium Clostridia botulinum and the closely related species *Clostridia butyricum* and *baratti*. When spores of the Clostridia botulinum are ingested they germinate and secrete BT that passes from the GI tract into the systemic circulation. The systemic spread of BT causes the disease botulism that is characterized by widespread neuromuscular paralysis.

BT is a protein consisting of a light and heavy chain that together weigh approximately 150 kilodaltons. BT works by a three-stage mechanism, binding, translocation into the neuron and molecular action, each of which is performed by separate 50 kilodalton domains. The binding and translocation domains make up the heavy chain, while the catalytic action is performed by the single domain of the light chain.

At present seven immunologically distinct serotypes of the BT are known, named A, B, C, D, E, F and G. The effect of BT is to inhibit the release of neurotransmitters and neuropeptides by neurons. Although all BT serotypes interfere with proteins that cause the exocytosis of synaptic vesicles from cells they each interfere with different proteins, or different parts of the same protein. In clinical use each serotype appears to differ in its potency in blocking different classes of neurons.

BT binds to specific molecules present on neuron presynaptic membrane. After binding it is internalized into the neuron by formation of an endosome. When the interior of the endosome becomes acidic, the light chain translocates across the membrane and is released into the cytoplasm. After translocation across the cell membrane the CT light chains cleave the proteins involved in synaptic vesicle docking and release that are collectively known as SNARE proteins. The targets of the CT are the following:

BT A & E cleave SNAP-25 (synapse associated protein)
BT C cleave SNAP-25 and syntaxin
BT B, D, F & G cleave VAMP (vesicle associated membrane protein)

The vesicles within neurons contain classical neurotransmitters (acetylcholine, epinephrine, nor epinephrine, dopamine, serotonin, glutamate, GABA and others) and/or neuropeptides (substance P, neurokinin A, calcitonin gene related peptide (CGRP), neuropeptide Y, interleukins, growth factors and others). BT has been shown to block secretion of all these molecules.

The Clinical Effects of Botulinum Neurotoxin

Voluntary Motor Nerves

The first and still primary use of BT is to block motor nerve communication with muscle fibers. BT is injected within the target muscle. The BT is then internalized into motor neurons where it decreases or stops the release of the neurotransmitter acetylcholine (AChE), thereby causing paresis or paralysis of the muscle. Scott introduced the concept of localized muscular injections of BT for the specific condition of strabismus (squint, crossed eyes). Later BT was found to be particularly useful for movement disorders such as tics, spasms, contractures, cramps and tremors. More recently, the injection of BT into facial muscles has been found to ameliorate skin wrinkling and lines related to aging. Another recent application of BT injections is to decrease the pain accompanying muscle tension in conditions such as headache and temporomandibular joint syndrome.

Autonomic Motor Neurons

The autonomic nervous system is divided into a parasympathetic system and a sympathetic system. The parasympathetic neurons use acetylcholine as their neurotransmitter and they can be blocked with BT. The sympathetic nervous system uses noradrenaline as its neurotransmitter with the single exception of sweating) and this neurotransmitter is not blocked by BT. Effector neurons of the parasympathetic system innervate and control the contraction of smooth muscles. Injections of BT have been used to decrease tone in the smooth muscles of the lower esophageal sphincter, esophagus, stomach wall, and pyloric sphincter, sphincter of Odi, anal sphincter, and urinary bladder.

Autonomic Secretory Neurons

In addition to their innervation of smooth muscle, neurons of the autonomic system control or modulate a wide variety of other functions such as the secretion of various glands throughout the body. BT injections have been used to decrease gastric secretions including acid production, nasal and other respiratory secretions, and tearing.

Neuropeptides

In addition to the neurotransmitters released at localized synaptic sites, many autonomic and sensory nerves can release neuropeptides along part or all of the length of the axons. These peptides are most noticeable in skin as mediators of inflammation, allergic reactions and pain. For example injury in a small area of skin causes reflex vasodilation in surrounding areas. These reactions are neurally mediated and depend on the release of neuropeptides. Although the neurogenic vasodilation of skin is blocked by BT, whether other phenomenon such as pain and swelling are blocked is still controversial.

Tetanus Toxin

Tetanus toxin (TT) is produced by the *Clostridium tetani* bacterium. When *Clostridium tetani* spores infect wounds they germinate and produce TT. The TT is taken up by peripheral nerves near the wound and transported retrograde to the central nervous system. It then spreads by diffusion and further neural transport. At low doses TT blocks release of the inhibitory neurotransmitters GABA and glycine causing increased activity in motor and autonomic nerves. Clinically the condition is called tetanus and is characterized by severe muscular spasms and autonomic instability. However, at higher doses TT blocks all neurotransmission and clinically this appears as a flaccid paralysis.

TT also works by a two-stage mechanism that is similar to BT. However; the major difference is that after the peripheral neuron internalizes the TT via endosomes the TT is not released into cytoplasm. Instead the endosomes are actively transported back to the cell body of the neuron. Here TT is again released into all synapses. At low doses the blocking is selective for inhibitory neurons. However at higher doses TT blocks all neurons both inhibitory and excitatory, centrally and peripherally.

TT also differs from BT in that it is taken up by more classes of neurons and at lower doses then BT. As described above the effect of excitation or inhibition of a given neuron by TT are dose related. Peripheral block of a neuron requires 10-1000 times the dose that causes excitation of that same neuron. However, hybrid molecules of TT, such as those that combine the heavy chain of BT with the light chain of TT, could be expected to have the same dose effects of as whole BT.

Skin Secretory Glands

Secretion is the combined result of production of secretion by specialized cells within a skin gland, and the expulsion of the secretion from the gland and ducts by contraction of surrounding muscle-like myoepithelial cells. In some secretory glands, such as the mammary gland, increased expulsion has a feed back effect in stimulating further secretory production. In addition, the number and amount of secretory and myoepithelial cells can be modulated, with proportional changes in the amount of secretion produced. Finally the act of secretion is often accompanied by vascular dilation around the gland, which is believed to aid the gland by increased delivery of nutrients.

Skin secretory cells produce their secretion by 3 basic mechanisms.

Apocrine glands are the common sweat glands present throughout the skin surface that produce profuse watery secretion. Apocrine glands have a simple organization; the gland is composed of a coiled duct in the dermis with an open end that discharges onto the skin surface. They produce a watery secretion that evaporates and cools the skin thereby playing a role in thermoregulation. Discharge of the secretion from the lumen of the ductal portion of the apocrine sweat gland is assisted by the action of myoepithelial cells which surround the secretory portion of the gland.

The cells lining the ducts of apocrine glands produce the secretion by a merocrine mechanism. This terminology is confusing as it would appear that this sweat glands should be called merocrine glands. However, the sweat glands were named before the exact mechanism of their cellular secretion was known, and their original names have persisted.

Excessive sweating, formally known as hyperhydrosis, is a common condition. Hyperhydrosis can occur in any part of the body but primarily affects the forehead, axilla, palms and feet. Sanders and Shaari (U.S. Pat. No. 5,766,605) Walker (U.S. 20020086036) disclose a method of treating hyperhydrosis using needle and jet injections of BT.

Eccrine glands are commonly thought of as specialized sweat cells that produce a secretion with high protein content. Eccrine sweat glands are found in the axilla, in the areolae of the breast and around the anus. They are larger than apocrine sweat glands and produce a viscous secretion into hair follicles. The secretion released by apocrine sweat glands is odorless but the bacteria metabolize the secretion and decompose it's proteins, thereby causing a strong odor, which is usually experienced as unpleasant.

WO03026602A2: Medicine For Preventing And Treating Bromidrosis discloses the use of BT injections of BT for decreasing the odor of sweat.

Holocrine glands are fundamentally different from apocrine and eccrine glands. The secretion is primarily lipid rather than water. Moreover the lipid secretion is not secreted from cells; instead the cell, called acebocyte, accumulates large amounts of the secretion and then dies, releasing the lipid material together with cellular remnants.

The vast majority of holocrine glands are sebaceous glands that produce a lipid secretion called sebum. Sebaceous glands usually have several acini that open into a short duct. The sebum producing cells are present in the acini and in the wall of the duct. Most sebaceous glands are called pilosebaceous glands because they secrete into a duct that normally opens into the upper part of a hair follicle. However, in certain areas of the body such as the lips the ducts open directly onto the skin's surface. A variety of other holocrine organs are present in the skin of the eyelids: meibomium glands, and glands of Zeiss and Moll.

The control of holocrine glands has long been known to involve systemic hormones, particularly the male sex hormones called androgens. Androgens increase during puberty in both males and females. Supporting the connection between hormones and sebaceous gland function is that sebum production increases after puberty and its peak incidence is from ages 12 to 22. Increased sebum production is also related to pregnancy, pre-menstrual period and to birth control medication.

The role of classical neurotransmitters such in sebum production is unclear. Anticholinergics appear to have little effect on sebum production. However, pilocarpine, a cholinergic agonist, increases sebum production when iontophoresed across the skin (Yosipovitch et al, Br J Dermatology, 1995: 561-4). Evidence suggests that increased sebum production in response to cholinergics may be due more to expulsion of accumulated sebum rather then increased cellular secretion. Even facial movement seems to be important in emptying accumulations of sebum as patients with facial paralysis accumulate greater amounts of sebum.

Dopamine appears to play an inhibitory role in sebum secretion as patients with Parkinson's disease, a disease in which central nervous system levels of dopamine are low, have been reported to have increased sebum production.

Treatment of these patients with dopaminergic drug therapy appears to decrease sebum levels whereas anticholinergic drugs have no effect (Villares, Arq Neuropsiquiatr, 1989, 47: 31-8). However, the dopaminergic effects on sebum production may be within the central nervous system, or to increase facial movement as untreated Parkinson's patients have decreased facial movement.

Recent research has shown that surprisingly, holocrine secretion is controlled by various neuropeptides, with substance P playing a significant role (Toyoda and Marohashi, Med Electron Microsc 2001, 29-40). Other neuropeptides found in neurons surrounding sebaceous glands include NPY, VIP and ENK, although their roles are unclear.

Mixed glands are skin secretory glands in which holocrine components are mixed with apocrine or eccrine components. Holocrine components have been reported in the cerumen glands that produce ear wax (Main and Lim, Laryngoscope, 1976, 86:1164-76) and mammary glands that produce milk.

Clinical Conditions Affecting Holocrine Glands

Acne Vulgaris

One of the most common disorders of the sebaceous glands is Acne Vulgaris (acne). Acne is largely a disease of adolescence and young adulthood characterized by inflamed glands within the skin of the face, shoulders, and back. It is estimated that almost all people suffer at least some acne during their lives.

Excessive sebum production within pilosebaceous glands results in an enlarged and obstructed sebum gland. These obstructed glands are highly susceptible to infection by Propionibacterium acnes (P. acnes) causing an inflamed pustule called a comedone. These inflamed pilosebaceous glands can cause permanent scaring of skin.

Current therapy of acne includes topical and oral agents. Topical retinoic acid is the treatment of choice for non-inflammatory acne. Benzoyl peroxide and/or topical antibiotics are used to treat inflammatory acne including papules pustules and cyts, systemic antibiotics are also used for inflammatory acne.

Systemic therapy consists mainly of systemic antibiotics, usually tetracycline, to decrease bacteria until the patient is in remission; then a lower dose is used for maintenance. Oral isoretinoin inhibits sebaceous gland function and keratinization by an unknown mechanism. However due to its severe side effects, including liver disease and birth defects, its 16-20 week course is reserved for severe acne unresponsive to conventional therapy.

Seborrheic Dermatitis (Seborrhea)

Seborrhea is an acute or subacute skin disorder of unknown etiology presenting as eruptions in skin areas containing many sebaceous glands. The scalp and face are most common and may result in hair loss (alopecia). Lesions are red to yellow and may be itchy and scaly. Treatment includes removal of scales with frequent washing and shampooing with selenium sulfide suspension, zinc pyrithione, or tar and salicylate shampoo.

Sebaceous Cyst

Obstruction of a single sebaceous gland may result in a intra dermal cyst. These can occur anywhere on the body and become infected and form abscesses. Treatment includes oral antibiotics, surgical drainage and/or excision of the cyst.

Seborrheic Blepharitis (Blepharitis)

The holocrine glands of the eyelid are called mebomium glands. They produce an oily substance that aids in lubricating the exposed surface of the eye. Blepharitis is an acute to chronic condition that presents as a burning and itching of the eyelids. Signs are waxy scales on the eyelashes, loss of eyelashes, and lid ulceration and secondary infection with Staphylococcus aureus.

Treatment includes meticulous hygiene, mild shampoo, and topical antibiotics.

Rosacea and Rhinophyma

Although the cause of rosacea is unknown, it is closely associated with and involves sebaceous glands. Rosacea is a chronic condition that begins as periodic facial flushing and progresses to telangestasia, papules, pustules and nodules. It is more severe in men and often associated with rhinophyma, thickened bulbous skin of the nose. Treatment of acne like rosacea includes topical or systemic antibiotics, topical steroids and Sulfacet-R lotion.

Furuncles, Carbuncles, Pustules, Chalazions, and Styes

Skin infections often begin in pilosebaceous glands. In acne the infectious bacterium is P. acnes. However many conditions begin with an inflamed pilosebaceous gland and are secondarily infected with other bacteria such as *Staphylococcus aureus* and *Streptococcus epidermis*. Single small infections are called furuncles, larger ones are called pustules and when subdermally spread to create large fluctuant abscesses called carbuncles. In the eye, analogous infections of the specialized holocrine glands are called styes and chalazions. Treatment of these conditions includes warm compresses, topical and systemic antibiotics, and often surgical drainage.

Excessive Sebum

More of a cosmetic condition then a medical one, excessive sebum production is quite common. Most often the central area of the face is affected, and this area looks and feels greasy. Treatment is frequent washing of the face with strong soaps. This often causes secondary drying of the remaining areas of the skin.

Excessive Cerumen

Cerumen is produced by mixed holocrine like glands in the skin of the ear canal and its production is at least partly under cholinergic control. Cerumen normally slowly migrates outward and is lost from the meatus of the ear canal. In some patients cerumen accumulates within the ear canal, sometimes to the point of impaction. This can cause underlying infection of the ear canal called otitis externa and decreased hearing due to poor sound transmission. Treatment includes cerumen dissolving chemicals such as carbamide peroxide and/or manual removal of the wax by a physician.

Mammary Secretion

During and after pregnancy the mammary gland produces breast milk. Although lactation is principally hormonal the secretion and expulsion is influenced by neurotransmitters. Cattle with low grade botulinum toxin poisoning have been noted to have dramatically decreased milk production despite normal appetites.

Lactation is natural and necessary for breast feeding the newborn. However not all mothers wish to breast feed, and in cases of miscarriage or stillborn the presence of breast fluids is a painful psychological reminder of the loss. Finally the increase in size of the breast during the pregnancy and post partum period eventually involutes, contributing to a cosmetic undesirable loss of tone in breast tissue.

U.S. 20020094339A1: Methods For Treating Mammary Gland Disorders discloses the use of CT to decrease the size of mammary glands and secondarily decrease the incidence of mammary malignancies.

At present there is a large need in the art for compositions and methods of inhibiting secretions of holocrine glands.

OBJECTS AND SUMMARY OF THE INVENTION

The present invention is directed to methods of controlling excessive levels of secretions from glands selected from the group consisting of holocrine glands, cerumen glands and mammary glands in patients by administering to said patient a secretorily controlling amount of botulinum toxin. Such administration is particularly effective in the thinning the skin as well as smoothing of fine (as opposed to gross) wrinkles in the skin. It is also directed to the formulation of compositions for specifically carrying out such secretion control.

Administration may be by methodologies generally known to those skilled in the art such as topical and by injection, suitably subdermal, intradermal, transdermal and intramuscular injection. It should be noted that the terms "dermal" and "cutaneous" are considered mutually equivalent.

Suitably, injection of botulinum toxin A is carried out at multiple sites in the skin, wherein the sites of adjacent injections are separated by about 0.1 to 10 cm., suitably about 0.5 to about 5 cm. preferably by about 1.5 to about 3 cm. The toxins may be any of the botulinum toxins A,B,C,D,E,F or G. The amounts administered may vary between 0.1 and 1000 U, suitably about 1 to about 40, often from about 5 to about 10 U, depending on the manufactures specifications, the class of the toxin and the mode of administration. Thus 1 U of Botox equals about 2-4 units of Dysport and about 20-40 units of Myobloc.

The separation of the distances between injections will vary from about 1 mm to about 10 cm, suitably from about 5 mm to about 5 cm, and more usually from about 1 cm to about 3 cm. Thus for example botulinum A may be suitably administered by intradermal injection between about 0.1 to about 10 U at a separation of from about 0.5 to about 10 cm. preferably at about 2.5 cm. Botulinum B may be administered in the range of 1-500 U, preferably 100 U separated by 1.5 cm.

The repeat time range for these injections for maintenance of the desired change varies substantially according to the location of the injection, the condition to be adjusted and the condition of the patient. Thus the repeat time may vary from about 1 week to about 50 weeks, a common range is about 4 to about 25 weeks, or even about 12 weeks to about 16 weeks.

These numbers are to be considered for exemplification and not limitation. Administration within any of the foregoing methods, amounts and separations may be established by one skilled in the art without undue experimentation for particular circumstances.

It is an object of the invention to provide compositions and methods for the use of CT as treatment for clinical and cosmetic disorders of the skin.

It is another object of this invention to treat dysfunction of holocrine glands and related secretory structures in human skin with local applications or injections of therapeutically effective amounts of CT or similar biologic agents to decrease the number and/or activity of axons that either directly or indirectly modulate the activity of these glands.

It is an object of this invention to provide a treatment of skin disorders related to secretions of holocrine glands and related structures, examples given without limitation the following: to decrease production of secretion by blocking neural excitation of the secretory cells, the contractile components that express the secretion from glands, the neural effects on glandular size, related skin cell changes, and the supply of fluid and nutrients by neural excitation. Holocrine glands include sebaceous glands, pilosebaceous glands, meibomium glands, glands of Zeiss and Moll, and the holocrine-like components of cerumen and mammary glands.

Conditions of excessive sebum production include acne vulgaris, seborrheic dermatitis, rosacea, rhinophyma, seborrheic blepharitis, sebaceous cysts, excess cerumen, and unwanted milk production. A second beneficial effect is to decrease bacterial infections of these glands by decreasing the amount of secretion available for infection. Infectious conditions include hidradenitis, furuncles, carbuncles, styes and chalazions. A third beneficial effect is to decrease gland size and production and related skin cell reactions for cosmetic benefit. Cosmetic conditions include mammary hypertrophy and to smooth skin and decrease the size of skin surface pores.

DETAILED DESCRIPTION OF THE INVENTION

Sebum production and related disorders such as acne have long been thought to be under the control of systemic hormones. Unexpectedly it has been found that intradermal injection of CT decreases sebum production. The ability to decrease sebum production allows for the treatment of a variety of new conditions that were not previously treatable with CT.

Moreover, without wishing to be bound by this theory, the mechanism by which CT decrease sebum production is by decreasing the release of the neuropeptide substance P.

By "Clostridia neurotoxins (CT)" it is meant the botulinum neurotoxin serotypes A-G produced by *Clostridia botulinum, baratii,* and butyricum and tetanus toxin produced by *Clostridia tetani* and other natural toxins with similar biologic effects, particularly the proteolytic effects on SNARE proteins. The scope of the invention is meant to include modifications where the modified CT or fragment thereof retains essentially similar biological action as the wild type CT. Modifications include, without limitation:

Hybrid CT that combine heavy and light chains, or fragments of those chains, from different BT serotypes and TT.

Substitution of CT binding domain with, or the addition to the CT of binding domains from other bacterial toxins or viruses, ligands for cell membrane receptors, antibodies or antibody fragments, combine fragments of different CT either with each other or with binding and/or translocation domains of other bacterial toxins.

Substitution of the CT translocation domain, or addition to the CT of translocation sequences from other bacterial toxins, or chemically constructed translocation domains, or membrane transfer proteins such as the TAT sequence.

Addition, substitution or subtraction of amino acids or chemical modification of amino acid side chains.

Recombinant forms of CT.

Delivery within the skin cells of nucleic acid coding for CT.

By "therapeutically effective amount" it is meant of purposes of this invention that the CT is administered in a nontoxic amount sufficient to cause reduction in the occurrence or magnitude of the symptoms being targeted. At present CT is measured by biological assay; a unit of BT is the amount that causes death to 50% of mice when injected intraperitoneally. BT A is marketed as Botox by Allergan Corp, Irvine Calif., and as Dysport by Ipsen Ltd, Berks United Kingdom. BT B is marketed as Myobloc by Elan Pharmaceuticals, Dublin, Ireland. Other BT serotypes are available from Metabiologics, Madison, Wis. TT is not marketed for human use but is from List Biological Labs (www.listlab.com).

A therapeutically effective amount of CT will vary depending on: the area of skin to be treated as injections diffuse about 2 cm; the method of application; the serotype of toxin used (approximately 20-40 BT-B units have the same effects as one BT-A unit in human clinical applications); the exact preparation of the serotype (potency of BT-A from the two commercial vendors varies. The same clinical effect requires 2-4 times the dose of Dysport (frpm Ipsen) than Botox, the BT-A formulation, from Allergan). At present the use of BT-A for muscle indications varies from about 1 unit (eye and larynx muscles) to hundreds of units (limb and major neck muscles). The exact dosage will not require undo experimentation by those skilled in the art. (Saltzman M: Drug Delivery, (2001) Oxford University Press, New York, N.Y., Transdermal Drug Delivery Guy RH (editor) Marcel Dekker; (2003)).

DETAILED DESCRIPTION OF PREFERRED EMBODIMENTS

A detailed method of CT application to reduce sebum production will be disclosed and examples will be given to disclose minor variations for different specific conditions.

EXAMPLE 1

Sebum Secretion Assay

Sebum secretion was assayed by application of fine blotting paper to forehead skin. The skin area was first wiped with moist and dry cloths to remove any skin secretions. Blotting at this time was negative. Two sheets of blotting paper were placed on both sides of forehead and an elastic band was then placed around the forehead to gently press the blotting paper onto the skin. After 2 hours the blotting papers were removed, allowed to dry and then transilluminated. Areas where sebum secretion occurred were significantly darker then the unstained areas. The pattern of non-injected forehead skin was the of a circular areas of approximately 0.25 to 0.5 cm in diameter that overlapped extensively resulting in an almost complete dark band 4 cm wide across the forehead.

A 49 year old male was injected with 100 units of botulinum toxin B (Myobloc, Elan, Dublin) The injection was made with a size 26 needle attached to a 1 cc syringe. The skin of the right forehead was cleaned with alcohol and the needle injection was placed into the center of the right forehead, equidistant from the eyebrow and hairline. The tip of the needle was advanced through the skin surface and injection was made intradermally. A white raised bleb approximately 0.5 cm in diameter was seen at the site of injection.

Directly after toxin injection, no change in blotting pattern was seen from uninjected patterns. One day after injection a repeat assay showed that a clear area was present at the site of injection with a diameter of approximately 1 cm. On the second day after injection the area had increased to a maximum of 1.5 cm. The cleared area gradually decreased in size and was not detectable at 2 months. In all trials the uninjected side did not show any clear areas.

In another experiment on the same subject, 10 units of Botulinum A (Botox) at a dilution of 2.5 units per 0.1 cc of saline was injected intradermally into the mid forehead. After one day a clear area was found after blotting with a maximum diameter of approximately 2.5 cm. Blotting showed a decrease in area by 50% by 2 months and was not detectable at 4 months.

One surprising observation was that the injected area became noticeably smoother within a few days after injection. This smooth appearance was due to smaller and less noticeable skin pores as well as thinning of the skin, and a decrease in the fine wrinkling of the skin surface. Both the flattening and smoothing effects lasted as long as the deceased sebum secretion and the skin texture returned to its former condition after the other effects also disappeared. This smoothing is distinct from the decrease in the larger skin wrinkles that occurs after facial skin is immobilized by botulinum toxin injection into facial muscles of expression. The etiology of these effects on skin texture are unknown. However, without wanting to be bound by theory it may be due to atrophy of skin glandular elements and associated tissue due to denervation by the botulinum toxin.

EXAMPLE 2

Acne Vulgaris

The target glands are sebum glands of the face, shoulders and back. BT would be topically applied or injected so as to bind to the neurons stimulating the pilosebaceous glands and associated structures, thereby decreasing the production and/or accumulation of sebum. This could be done as treatment for exacerbations of the disease or as a preventive measure during quiescent periods.

A patient with a long history of acne vulgaris presents with multiple comedones of both cheeks. Five injections of 2 units of BT-A are injected intradermally into separate site of each cheek for a total of 20 units.

EXAMPLE 3

Seborrheic Dermatitis

A patient with seborrheic dermatitis presents with a widespread rash on her face and scalp associated with alopecia. Twenty injections of 2 units of BT-A (total of 40 units) in injected into multiple sites involved in the disorder including the area of hair loss.

EXAMPLE 4

Sebaceous Cyst

A patient presents with a 1 centimeter mildly tender sebaceous cyst within the skin of the right inner thigh. A single injection of 5 units of BT-A is made into the cyst.

EXAMPLE 5

Rosacea and Rhinophyma

A patient with chronic rosacea and rhinophyma presents for treatment. Ten intradermal injections each containing 2 units of BT-A (total 20 units) are made at various places of the mid face, and five additional injections are made directly into the skin of the nose.

EXAMPLE 6

Blepharitis

A patient with chronic blepharitis of the eyelids of both eyes. The patient receives a single injection of 0.5 units of BT-A to the edge of each eyelid (total 2 units).

EXAMPLE 7

Bacterial Infections

A patient with a history of recurrent eyelid chalzions applies topical ointment containing 10 units of BT-A per cc is daily along with warm compresses.

EXAMPLE 8

Skin Texture Smoothing

A patient has significant fine wrinkling of her facial skin that she feels is cosmetically objectionable. She undergoes topical application of 50 units of BT-A in a cream form to the skin of her forehead, periorbital region and cheeks.

The forgoing suppression of fine wrinkling is also by achieved by the intradermal injection of BT suitably at multiple but adjacent sites by the injection of between 1 and 100 units of BT at separations of between 0.5 to 10 cm. BT-A is preferred but BT-B (as well as BTC-BTG) may also be used.

Repetition of treatment at intervals of about 3 to about 6 months is desirable.

EXAMPLE 9

Excessive Sebum

A patient has excessive sebum of the face requiring twice daily cleansing with special soaps that dry her skin, 10 injections, each of 100 units of BT-B are injected into the skin of the eyebrows, forehead, and nose and nasolabial folds.

EXAMPLE 10

Unwanted Lactation

A female patient has post partum depression following a stillborn birth. To decrease the production of breast milk 3 injections of 20 units of BT-A are made into each breast (120 units total).

EXAMPLE 11

Mammary Hypertrophy

A female patient with perceived mammary hypertrophy learns she is pregnant. Not wishing further enlargement of the breast during pregnancy she receives 3 injections of 20 units of BT-A are made into each breast (120 units total).

Example 12

Skin Cosmesis

A patient perceives that the skin of her nose has large pores related to pilosebaceous glands. She is injected with two injections of 5 units of BT-A (10 units total) to the skin overlying the nasal alae) In one month the size of the skin pores has decreased by 50%.

EXAMPLE 13

Cerumen Blocking

A male patient experiences cerumen impaction every 6 months. Each ear is injected with 5 units of BT-A into the skin at the junction of the bony and cartilaginous canals.

REFERENCES

Abstracts of the International Conference 2002 Basic and Therapeutic Aspects of Botulinum and Tetanus Toxins, Hannover, Germany, Jun. 8-12, 2002

Braune C, Erbugh F. Birklein F: Dose thresholds and duration of local anhidrotic effect of botulinum toxin injections measured by sudometry. Br J Dermatol (2001) 144:111-7.

Chung C W. Tigges M, Stone R A. Peptidergic innervation of the primate meibomian gland. Invest Opthalmol Vis Sci (1996) 37 (1): 238-45.

Gibbins 1 L: Target-related patterns of co-existence f neuropeptide Y, vasoactive intestinal peptide, enkephalin and substance P in cranial parasympathetic neurons innervating the facial skin and exocrine glands of guinea-pigs. Neuroscience. (1990) 38 (2); 541-60.

Main T, Lim D: The human external auditory canal, secretory system—an ultrastructural study. Laryngoscope. (1976) 86 (8):1164-76.

Massura M: Clostridia botulinum and botulin. FVO magazine June 2002

Muraki R, Iwasaki T, Sata T, Sato Y, Kurata T: Hair follicle involvement in herpes zoster: pathway of viral spread from ganglia to skin. Virchows Arch (1996) 428 (4-5):275-80

Rossettoa O, Sevesoa M, Caccina P, Schiavob G, Montecuccoa C: Tetanus and botulinum neurotoxins: turning bad guys into good by research Toxicon (2001) 39:27-41

Ruocco I, Cuello A C, Shigemoto R, Ribeiro-da-Silva A: Light and electron microscopic study of the distribution of substance P-immunoreactive fibers and neurokinin-1 receptors in the skin of the rat lowerlip. (2001) J Comp Neurol 432 (4):466-80.

Scott A B: Botulinum toxin injection of eye muscles to correct strabismus. Trans Am Opthal Soc, (1981) 179:734-770

Simons E, Smith P G: Sensory and autonomic innervation of the rat eyelid: neuronal origins and peptide phenotypes. J Chem Neuroanat (1994) 7 (1):35-47.

Thody A J, Shuster S: Control and Function of Sebaceous Glands Physiological reviews (1989) 69:2, 383-416

Toyoda M, Morohashi M: Pathogenesis of acne. Med Electron Microsc (2001) March 34:29-40

Villares J C: L-dopa, biperiden and sebum excretion in Parkinson's disease. Arq Neuropsiquatr 1989 47:131-8.

Yosipovitch G, Reis J, Tur E, Sprecher E, Yarnitsky D, Boner G. Sweat secretion, stratum hydration, small nerve function and pruritus in patients with advanced chronic renal failure. Br J dermatol 1995 133 (4) 561-4

Transdermal Drug Delivery Guy R H (editor) Marcel Dekker; (2003)

Drug Delivery, Saltzman W H Oxford University Press, (2001)

WO02/00172 Methods for using Tetanus Toxin for beneficial purposes in animals.

U.S. 20020086036A1: Methods for treating hyperhydrosis

U.S. 1998 U.S. Pat. No. 5,766,605: Treatment of autonomic dysfunction with botulinum toxin.

WO03/011333A1 botulinum toxin in the treatment or prevention of acne

The invention claimed is:

1. A method of smoothing fine wrinkles in the skin and thinning the skin of a subject in need of such treatment which comprises administering to the dermis of said patient a therapeutically effective amount of Botulinum toxin, whereby said fine wrinkles are smoothed.

2. The method of claim 1 wherein the administration is topical.

3. The method of claim 2 wherein the Botulinum toxin is Botulinum toxin A.

4. The method of claim 1 wherein the administration is by intradermal injection.

5. The method of claim 4 comprising injection at multiple sites in the skin, wherein the sites of adjacent injections are separated by about 0.5 to 10 cm.

6. The method of claim 5 wherein the sites of adjacent injections are separated by about 1.5 to about 3 cm.

7. The method of claim 4 wherein the amount injected is between 1 and 100 U of Botulinum toxin.

8. The method of claim 7 wherein the amount injected is between 1 and 10 U of Botulinum toxin.

9. The method of claim 8 wherein the amount injected is between 2 and 3 U of Botulinum toxin.

10. The method of claim 4 wherein the Botulinum toxin is Botulinum toxin A.

11. The method of claim 1, wherein said method is repeated periodically to inhibit the recurrence of undesirable levels of wrinkling.

12. The method of claim 11 wherein said method is repeated at intervals of from about 3 to about 6 months to inhibit said recurrence.

13. The method of claim 11 wherein said method is repeated at intervals of about 4 months to inhibit said recurrence.

14. The method of claim 1, wherein the Botulinum toxin is Botulinum toxin B.

15. The method of claim 1, wherein the Botulinum toxin is Botulinum toxin C.

16. The method of claim 1, wherein the Botulinum toxin is Botulinum toxin D.

17. The method of claim 1, wherein the Botulinum toxin is Botulinum toxin E.

18. The method of claim 1, wherein the Botulinum toxin is Botulinum toxin F.

19. The method of claim 1, wherein the Botulinum toxin is Botulinum toxin G.

* * * * *